(12) United States Patent
Velde

(10) Patent No.: US 7,067,721 B2
(45) Date of Patent: Jun. 27, 2006

(54) HYBRID ALFALFA VARIETY NAMED HYBRIFORCE®-420/WET

(75) Inventor: Michael J. Velde, Clinton, WI (US)

(73) Assignee: Dairyland Seed Co., Inc., West Bend, WI (US)

( * ) Notice: Subject to any disclaimer, the term of this patent is extended or adjusted under 35 U.S.C. 154(b) by 0 days.

(21) Appl. No.: 10/798,517

(22) Filed: Mar. 10, 2004

(65) Prior Publication Data

US 2005/0204434 A1 Sep. 15, 2005

(51) Int. Cl.
*A01H 5/00* (2006.01)
*A01H 4/00* (2006.01)

(52) U.S. Cl. ........................................ 800/298; 435/410
(58) Field of Classification Search ................ 800/260, 800/265, 266, 271, 274, 298, 301, 302, 303; 435/410

See application file for complete search history.

(56) References Cited

U.S. PATENT DOCUMENTS

| | | | |
|---|---|---|---|
| 3,570,181 A | 3/1971 | Davis | 47/58 |
| 4,045,912 A | 9/1977 | Sun | 47/58 |
| 6,005,165 A * | 12/1999 | Dobrenz et al. | 800/260 |

OTHER PUBLICATIONS

Viands et al. 1988. Pollination control: mechanical and sterility, pp. 931-960, In Alfalfa and alfalfa improvement, Agronomy Monograph No. 29, Crop Sci. Soc. of America, Madison, WI.*

Hay & Forge Grower (http://hayand forage.com/mag/farming_product_review_7).*

"Standard Tests to Characterize Alfalfa Cultivars", North American Alfalfa Improvement Conference, 3rd Edition, (1996). http://www.naaic.org/stdtests/index.html.

Hybrid Alfalfa Certification Standards. Genetic and Crop Standards of the AOSCA (2001) p. 2-4 through 2-6.

Viands, D. R., Sun, P., and Barnes, D. K., 1988. Pollination Control: Mechanical and Sterility. Alfalfa and Alfalfa Improvement. ASA, CSSA, SSSA; Agronomy No. 29 pp. 931-960.

Richards, L.A. (ed), 1954. Diagnosis and improvement of saline and alkali soils. USDA Agric. Handb. 60. U.S. Government Printing office, Washington D.C.

Bernstein, L., and L.E. Francols. 1973. Leaching requirement studies: sensitivity of alfalfa to salinity of irrigation and drainage waters. Soil Sci. Soc. Am. Proc. 37:931-943.

* cited by examiner

Primary Examiner—David H. Kruse
Assistant Examiner—Keith O. Robinson
(74) Attorney, Agent, or Firm—Rider Bennett, LLP

(57) ABSTRACT

A hybrid alfalfa variety designated HybriForce®-420/Wet and deposited as ATCC Accession Number PTA-5858. Also disclosed is a hybrid alfalfa plant or part thereof derived from the seed deposited as ATCC Accession Number PTA-5858. This variety also has an increased level of tolerance to saline soils within dormant alfalfa.

6 Claims, No Drawings

HYBRID ALFALFA VARIETY NAMED HYBRIFORCE®-420/WET

FIELD OF INVENTION

This invention is in the field of alfalfa breeding, and more particularly to an alfalfa variety designated HybriForce®-420/Wet.

BACKGROUND OF THE INVENTION

Alfalfa (*Medicago sativa*) is perhaps the most important of forage species, providing one of the most effective sources of biological nitrogen. It is often called the "Queen of Forages" because of its highly digestible fiber and excellent protein source. Alfalfa improves soil tilth making it ideal for crop rotation.

Alfalfa breeding programs historically emphasized improving pest resistance, persistence, forage yield and forage quality. Increases in forage yield and forage quality have resulted in limited improvement. For example, see U.S. Pat. No. 4,045,912, which is incorporated herein by reference.

Breeding programs have focused on maximizing heterogeneity of the variety to improve yield and maintain stability. Heterogeneity resulted in wider variability of phenotypic features such as plant type, development rate, flowering dates, fall dormancy and winter hardiness. Hybridization of alfalfa results in greater uniformity of described traits.

A significant acreage in the Western United States has saline soils. Alfalfa is sensitive to saline soils. Salt has a deleterious effect on the growth of alfalfa seedlings. Salt also affects growth and limits yields of alfalfa. Symptoms affect stem elongation more than leaf growth. Non-dormant alfalfas have been described with salt tolerance. For example, see U.S. Pat. No. 6,005,165, which is incorporated herein by reference. However, no dormant alfalfas have been described with tolerance to salinity.

SUMMARY OF THE INVENTION

The present invention provides a *Medicago sativa* hybrid seed or cultivated seed designated HybriForce®-420/Wet ((A833×B209×(942176)), and deposited under the terms of the Budapest Treaty on Mar. 9, 2004 with the America Type Culture Collection (ATCC), Manassas, Va, under Accession Number PTA-5858.

The present invention includes *Medicago sativa* hybrid plant or cultivated alfalfa derived from seed deposited under the Accession Number PTA-5858. The plant may be grown directly from seed deposited under Accession Number PTA-5858, or may be obtained indirectly from a plant grown directly from seed by any suitable means. The invention includes succeeding generations of plants derived from plants grown from the seed of Accession Number PTA-5858.

In another aspect, the present invention includes the pollen and ovule of a plant derived from the seed deposited under Accession Number PTA-5858.

This aspect also includes the parental genetics that derive HybriForce®-420/Wet. This includes the cytoplasmic male sterile clone (A833), maintainer line (B209) and pollinizer line (942176).

The present invention provides seed comprising at least 75% hybridism produced by the steps of: (a) crossing by controlled pollination cytoplasmic male sterile alfalfa plants with maintainer line alfalfa plants to produce cytoplasmic male sterile hybrid seed; (b) selectively harvesting seed from the cytoplasmic male sterile hybrid plants of step (a); (c) crossing male sterile hybrid alfalfa plants by male fertile alfalfa plants by allowing pollination of plants grown from the seed of step (b) and seed from male fertile alfalfa plants, the male sterile seed and male fertile seed planted at a ratio of about 4:1; and (d) non-selectively recovering the seeds from the pollinated alfalfa plants of step (c).

Optionally, the percentage hybridism can be verified using either genetic or morphological markers.

These and further objects and advantages of the present invention will become clearer in light of the following detailed description of an illustrative embodiment of this invention.

BRIEF DESCRIPTION OF THE DRAWINGS

Not applicable.

DETAILED DESCRIPTION OF THE PREFERRED EMBODIMENT

In one aspect, the present invention includes the hybrid alfalfa seed deposited under the Budapest Treaty on Mar. 9, 2004 with the American Type Culture Collection in Manassas, Va as Accession Number, PTA-5858 and plants or plant parts derived from the seed deposited as Accession Number PTA-5858.

By "plants or plant parts derived from the seed deposited as Accession Number PTA-5858", it is meant a plant that is grown directly from the seed deposited as Accession Number PTA-5858, or a plant that is obtained indirectly from a plant frown from the seed deposited as Accession Number PTA-5858. Plants obtained indirectly from a plant grown from the seed deposited as Accession Number PTA-5858 may be grown from a vegetative cutting, seed, callus or tissue culture obtained from a plant or plant part grown from the seed deposited as Accession Number PTA-5858 or a clonal plant thereof.

With respect to the description of the preferred embodiment of the present invention, the following terms are employed as described below:

A Line: A Cytoplasmic male sterile or genetic male sterile line used as a female line. The A line has a condition where pollen is absent or non-functional in the flowering plants while the female parts are functional.

B Line: An alfalfa plant that has viable pollen and is female fertile. When a B line pollinates an A line, the seed harvested from the A line will be predominately male sterile.

C Line: A C line is a male and female fertile line that can be used as the pollenizer.

Clone: A group of plants originating by vegetative propagation from a single plant.

Cytoplasmic male sterility: a condition resulting from failure to produce pollen, the condition being dependent upon hereditary units in the cytoplasm.

Hybrid: The first generation progeny of a cross between two individuals differing in one or more genes. The term hybrid in this document refers to a cross between a male sterile line and a pollenizer line in which at least 75% of the seeds are hybrids.

Inbred: Progeny of an alfalfa plant mated to itself.

Pollenizer: Same as C line.

Pollinator: Leaf cutting, honey or bumble bees.

Pollinate: The transfer of pollen from the anther to stigma.

P.P.I.: Male sterile lines may be identified by evaluating pollen production using the pollen production index (P.P.I.). The four distinct classes are:

1. Male Sterile Plant (MS)
   a. PPI Rating=0
   b. No visible pollen can be observed with the naked eye when flower is tripped with a black knife blade.
2. Partial Male Sterile Plant (PMS)
   a. PPI Rating=0.1
   b. A trace of pollen is found with the naked eye when flower is tripped with a black knife blade.
3. Partial Fertile Plant (PF)
   a. PPI Rating=0.6
   b. Less than the normal amount of pollen can be observed with the naked eye when flower is tripped with a black knife blade.
4. Fertile (F)
   a. PPI Rating=1.0
   b. Normal amounts of pollen can be observed when flower is tripped with a black knife blade.

Restorer: C line

The cytoplasmic male sterile (A line) alfalfa plants contain sterile cytoplasm and the non-restorer gene. The maintainer line (B line) is a male fertile and female fertile plant. When this plant is crossed to an A line, maintains the sterility of the cytoplasmic males sterile line in the progeny. The maintainer plant contains normal cytoplasm and non-restorer gene. Methods for identifying cytoplasmic male sterility and maintainer lines of alfalfa are known to those versed in the art of alfalfa plant breeding (e.g., see U.S. Pat. No. 3,570,181). The pollenizer line (C line) is both male and female fertile.

In the preferred embodiment, the method of the invention was performed using the following hybrid breeding procedure.

1. Selecting a male sterile A line from a cytoplasmic male sterile population. Selecting a maintainer B line from maintainer population. Selecting a pollenizer C line from a restorer population.
2. Growing the selected A and B lines from vegetative cuttings and cross pollinating using both honey bees and leaf cutting bees to produce hybrid male sterile breeder seed. Seeds are harvested from the cytoplasmic male sterile plants.
3. During the controlled pollination step, growing the cytoplasmic male sterile (A) line in separate rows from the (B) maintainer line. Pollen transferring insects such as leaf cutting bees and honey bees pollinate the alfalfa plants. Mechanically separating the cytoplasmic male sterile plants from the maintainer plants facilitates selective harvest of hybrid seed from the cytoplasmic male sterile plants.
4. The selected pollenizer plants were inter-pollinated by bees such as leaf cutting bees and honey bees to produce breeder and foundation seed. Harvesting this seed in bulk.
5. For production scale of hybrid seed, planting the breeder and foundation seeds in a ratio of about 4:1 male sterile to pollenizer. Plants grown from these seeds are inter-pollinated by leaf cutting bees or honey bees.
6. Seeds are bulk harvested from the plants grown in step 5, above.
7. The percentage of hybridism was determined using morphological markers. The verification system used for HybriForce®-420/Wet determined percentage hybridity using the following formula:

$$\% \text{ Hybridism} = \frac{1 - P.P.I. \text{ (Hybrid and Non-hybrid**)}}{1 - P.P.I. \text{ (Hybrid*)}} - P.P.I. \text{ } (A \times B^{*}) \times .595^{**}$$

*: Hybrid seed: ((A833×B209)×(942176)) from harvesting only the female plants.

**: Hybrid and Non-hybrid seed: ((A833×B209)×(942176)) from harvesting the bulk of female and male seed.

***: A×B: (A833×B209) seed

****: The ASOCA 2001 publication of hybrid alfalfa certification standards provides a correction factor of 0.595 for non hybrid seed produced from female plants from sibbing and selfing.

The percent hybridism for HybriForce®-420/Wet is 83.8% (Table 17).

Plant Maintenance

The A lines are maintained by vegetative cuttings. The maintainer line can be maintained by either vegetative cuttings or self-seed. Pollenizer lines can be maintained by vegetative cuttings or self-seed.

Selection Criteria

Each of the lines used in developing the HybriForce®-420/Wet have been selected for one or more agronomically desirable traits. These traits may include: resistance to diseases, insects and nematodes; greater forage and seed yield, increased persistence, improved forage quality, uniformity in growth rate and time of maturity.

Pollen Production Index

Four fertility classifications were: male sterile (MS), partial male sterile (PMS), partial fertile (PF), and fertile (F) were used for this project. The distribution of male sterile hybrid A833×B209 is 0.0857 averaged over 239 repetitions.

Disease, nematode and insect resistances of HybriForce®-420/Wet

The response of alfalfa plant hybrid HybriForce®-420/Wet ((A833×B209) times (942176)) to diseases, nematode and insects. These pests were evaluated according to the "Standard Tests to Characterize Alfalfa Cultivars, 3$^{rd}$ edition, as amended July 1998", approved by the North American Alfalfa Improvement Conference.

For each type of pest tested, each line of parents were assigned to one of five classes of resistance according to the percentage of resistant plants as follows:

| Class | % Resistant Plants |
| --- | --- |
| Susceptible | <6 |
| Low Resistant | 6–14 |
| Moderate Resistant | 15–30 |
| Resistant | 31–50 |
| High Resistant | >50 |

HybriForce®-420/Wet was found to be high resistant to: bacterial wilt (*Clavibacter michiganense*) (Table 2), Fusarium wilt (*Fusarium oxysporum*) (Table 3), Phytophtora root rot (*Phytophthora megasperma*) (Table 4), Northern root-knot nematode (*Meloidogyne hapla*) (Table 8), Stem nematode (*Ditylenchus dipsaci*) (Table 7); resistant to: anthracnose (*Colletotrichum trifolii*) (Table 1), Verticillium wilt (*Verticillium alboatrum*) (Table 5), *Aphanomyces* root rot (Race 1), (*Aphanomyces euteiches*) (Table 6), spotted alfalfa aphid (*Therioaphis maeulata*) (Table 10) and pea aphid (*Acyrthosipon pisum*) (Table 9).

Agronomic Characteristics of HybriForce®-420/Wet

HybriForce®-420/Wet is a moderately dormant variety similar to the fall dormancy 4 check (Table 12). Its winter survival is similar to the very winter hardy check (Table 15). Flower color of the male line in the Syn. 2 generation is 90% purple, 10% variegated with trace amounts of cream, white and yellow. Flower color of the female line in the F1 generation is 90% purple, 10% variegated with trace amounts of cream, white and yellow (Table 16). Hybri-Force®-420/Wet's forage yield performance is 6%, 18% and 23% better than Magnum V, Oneida VR and Vernal, respectively (Table 13). Its persistence is comparable to Magnum V and Magnum IV (Table 14). HybriForce®-420/Wet is salt tolerant similar to the salt tolerant check (Table 11).

The estimate of the percentage of the germplasm sources of HybriForce®-420/Wet is Turkistan (25%), Flemish (25%) and Unknown (50%) The procedures for maintaining seed stock:

The cytoplasmic male sterile, A line (A833) is maintained by vegetative cuttings.

The maintainer line, (B209) and pollenizer line (942176) is maintained by both vegetative cuttings and selfed seed.

Primary Use of HybriForce®-420/Wet:

The primary use of HybriForce®-420/Wet is hay, haylage, greenchop and dehydration.

Breeding Procedure and Genetic Sources of HybriForce®-420/Wet

Parent clones were selected out of forage yield plots and/or disease nurseries. These parent plants were tested for male sterility, maintaining and restoration ability. The parent plants were also progeny tested for one or more of the following traits: forage yield, stand persistence, forage quality, resistance to bacterial wilt, *Fusarium* wilt, *Phytophthora* root rot, anthracnose (Race 1), *Verticillium* wilt and *Aphanomyces* root rot (Race 1). The percentage of parent plants trace to Magnum (20%), and Dairyland experimentals (80%). Female seed was generated by crossing a female line by a maintainer line in field isolation and inter-pollinated by honey, leaf cutting and bumble bees near Sloughhouse, Calif. in 1995–2000 to produce female Breeder Seed. Female seed was kept separate each year to produce Breeder seed. Male Breeder seed (Syn. 1) was produced in 1997 near Sloughhouse, Calif.

Table 1 is a table comparing HybriForce®-420/Wet to other alfalfa varieties for resistance to Anthracnose (*Colletotrichum trifolii*).

Table 2 is a table comparing HybriForce®-420/Wet to other alfalfa varieties for resistance to Bacterial wilt (*Clavibacter michiganense*).

Table 3 is a table comparing HybriForce®-420/Wet to other alfalfa varieties for resistance to *Fusarium* Wilt (*Fusarium oxysporum*).

Table 4 is a table comparing HybriForce®-420/Wet to other alfalfa varieties for resistance to *Phytophthora* Root Rot (*Phytophthora megasperma*).

Table 5 is a table comparing HybriForce®-420/Wet to other alfalfa varieties for resistance to *Verticillium* Wilt (*Verticillium albo-atrum*).

Table 6 is a table comparing HybriForce®-420/Wet to other alfalfa varieties for resistance to *Aphanomyces* Root Rot (Race 1) (*Aphanomyces euteiches*).

Table 7 is a table comparing HybriForce®-420/Wet to other alfalfa varieties for resistance to Stem Nematode (*Ditylenchus dipsaci*).

Table 8 is a table comparing HybriForce®-420/Wet to other alfalfa varieties for resistance to Northern Root-knot Nematode (*Meloidogyne hapla*).

Table 9 is a table comparing HybriForce®-420/Wet to other alfalfa varieties for resistance to Pea Aphid (*Acyrthosipon pisum*).

Table 10 is a table comparing HybriForce®-420/Wet to other alfalfa varieties for resistance to Spotted Alfalfa Aphid (*Therioaphis maeulata*).

Table 11 is a table comparing HybriForce®-420/Wet to other alfalfa varieties for resistance to other alfalfa varieties for tolerance to saline soils.

Table 12 is a table comparing HybriForce®-420/Wet to other alfalfa varieties for fall dormancy.

Table 13 is a table comparing HybriForce®-420/Wet to other alfalfa varieties for forage yield.

Table 14 is a table comparing HybriForce®-420/Wet to other alfalfa varieties for persistence.

Table 15 is a table comparing HybriForce®-420/Wet to other alfalfa varieties for winter survival.

Table 16 is a table of HybriForce®-420/Wet's flower color.

Table 17 is a table describing the level of hybridism of HybriForce®-420/Wet.

TABLE 1

ANTHRACNOSE (Race 1)
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | R | 2001 | 1 | 38 | 43 | |
| 1. Saranac AR | R | | | 40 | 45 | |
| 2. Saranac | S | | | 0 | 0 | |
| | Test Mean: | | | 35 | 39 | |
| | L.S.D. (.05%) | | | 10 | | |
| | C.V. (%) | | | 15 | | |

Test conducted in field _____ Lab  X

TABLE 2

BACTERIAL WILT
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | HR | 2001 | 1 | 65 | 56 | |
| 1. Vernal | R | | | 49 | 42 | |
| 2. Narragansett | S | | | 1 | 1 | |
| | TestMean: | | | 61 | 56 | |
| | L.S.D. (.05%) | | | 29 | | |
| | C.V. (%) | | | 27 | | |

Test conducted in field  X  Lab _____

TABLE 3

FUSARIUM WILT
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | HR | 2001 | 1 | 58 | 57 | |
| 1. Agate | HR | | | 55 | 54 | |
| 2. MNGN-1 | S | | | 2 | 2 | |
| Test Mean: | | | | 62 | 61 | |
| L.S.D. (.05%) | | | | 16 | | |
| C.V. (%) | | | | 16 | | |

Test conducted in field  X   Lab ____

TABLE 4

PHYTOPHTHORA ROOT ROT
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | HR | 2001 | 1 | 49 | 54 | |
| 1. WAPH-1 | HR | | | 50 | 55 | |
| 2. Saranac | S | | | 5 | 6 | |
| Test Mean: | | | | 40 | 44 | |
| L.S.D. (.05%) | | | | 12 | | |
| C.V. (%) | | | | 12 | | |

Test conducted in field ____ Lab  X

TABLE 5

VERTICILLIUM WILT
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | R | 1999 | 1 | 42 | 37 | |
| 1. Vertus | R | | | 45 | 40 | |
| 2. Saranac | S | | | 5 | 4 | |
| Test Mean: | | | | 42 | 37 | |
| L.S.D. (.05%) | | | | 12 | | |
| C.V. (%) | | | | 19 | | |

Test conducted in field ____ Lab  X

TABLE 6

APHANOMYCES ROOT ROT (Race 1)
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | R | 2001 | 1 | 32 | 36 | |
| 1. WAPH-1 | R | | | 44 | 50 | |
| 2. Saranac | S | | | 0 | 0 | |
| Test Mean: | | | | 39 | 44 | |
| L.S.D. (.05%) | | | | 12 | | |
| C.V. (%) | | | | 14 | | |

Test conducted in field ____ Lab  X

TABLE 7

STEM NEMATODE
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | HR | 2001 | 1 | 71.1 | 65.9 | |
| 1. Vernema | HR | | | 64.7 | 60.0 | |
| 2. Ranger | S | | | 12.0 | 11.1 | |
| Test Mean: | | | | 54 | 50 | |
| L.S.D. (.05%) | | | | 18 | | |
| C.V. (%) | | | | 42.6 | | |

Test conducted in field ____ Lab  X

TABLE 8

**ROOT-KNOT NEMATODE - Species: *M. Hapla***
Test conducted by Dairyland Seed Research Int'l at Clinton, WI

| Variety | Resistance Class | Year Tested | Syn Gen | Unadjusted % R | Adjusted % R | Score |
|---|---|---|---|---|---|---|
| HybriForce ®-420/Wet | HR | 2001 | 1 | 76 | 91 | |
| 1. Nev Syn. XX | HR | | | 75 | 90 | |
| 2. Lahontan | S | | | 0 | 0 | |
| Test Mean: | | | | 78 | 94 | |
| L.S.D. (.05%) | | | | 31 | | |
| C.V. (%) | | | | 29 | | |

Test conducted in field ____ Lab  X

TABLE 9

PEA APHID
Test conducted by Dairyland Seed Research Int'l at Sloughhouse, CA

| Variety | Resistance Class | Year Tested | Syn Gen | Unadjusted % R | Adjusted % R | Score |
|---|---|---|---|---|---|---|
| HybriForce ®-420/Wet | R | 2003 | 1 | 54.8 | 46.4 | |
| 1. CUF101 | HR | | | 65.0 | 55.0 | |
| 2. Ranger | S | | | 10.0 | 8.4 | |
| Test Mean: | | | | 45.0 | | |
| L.S.D. (.05%) | | | | 16.8 | | |
| C.V. (%) | | | | 24.0 | | |

Test conducted in field ____ Lab  X

TABLE 10

SPOTTED ALFALFA APHID
Test conducted by Dairyland Seed Research Int'l at Sloughhouse, CA

| Variety | Resistance Class | Year Tested | Syn Gen | Unadjusted % R | Adjusted % R | Score |
|---|---|---|---|---|---|---|
| HybriForce ®-420/Wet | HR | 1999 | 1 | 45 | 38 | |
| 1. CUF101 | HR | | | 71 | 60 | |
| 2. Ranger | S | | | 2 | 2 | |
| Test Mean: | | | | 62 | 52 | |
| L.S.D. (.05%) | | | | 15 | | |
| C.V. (%) | | | | 21 | | |

Test conducted in field ____ Lab  X

TABLE 11

Salt Tolerance
Test conducted by Dr. Steve Smith at University of Arizona

| Variety | Resistance Class | Year Tested | Syn Gen | Total yield in grams/plant 115 mM NaCl | Total yield in grams/plant Control | NaCl/Control Yield Ratio |
|---|---|---|---|---|---|---|
| HybriForce ®-420/Wet | Tolerant | 2003 | 1 | 5.7 | 5.83 | .938 |
| 1. AZ-90NDC-ST | Tolerant | | | 5.72 | 5.94 | .963 |
| 2. AZ-88NDC | Susceptible | | | 5.7 | 7.72 | .738 |
| | Test Mean: | | | 4.92 | 5.77 | |
| | L.S.D. (.05%) | | | .816 | .875 | |
| | C.V. (%) | | | 18.7 | 21.7 | |

Test conducted in field _____ Lab  X _____

TABLE 12

The Fall Dormancy Data of HybriForce ®-420/Wet
1. Test data

| | | | | Score or Average Height | | | | | |
|---|---|---|---|---|---|---|---|---|---|
| | | Date Last | Date | | Check Varieties | | | | |
| Test Location | Syn Gen | Cut (Mo/Yr) | Measured (Mo/Yr) | This Variety | 1. Archer | 2. 5246 | 3. Legend | LSD .05 | CV % |
| Clinton, WI | 1 | September 2000 | October 2000 | 14.0 | 16.6 | 10.6 | 13.6 | 3.2 | 12.8 |

Scoring system used: Fall growth measured in inches
HybriForce ®-420/Wet is a moderately dormant variety similar to the fall dormancy 4 check (Legend).

TABLE 13

The Summarized Forage Yield Data of HybriForce ®-420/Wet

| | Data | | | | Total Yield (DM T/A) | | | | | |
|---|---|---|---|---|---|---|---|---|---|---|
| Test Location | Planted Mo/Yr | Syn Gen | Year Harvested | No. Cuts | 1. This Variety | 2 Magnum V | 3. Oneida VR | 4 Vernal | LSD .05 | CV % |
| Clinton, WI | May 1998 | 1 | 1999 | 4 | 6.3 | 6.05 | | | .40 | 5.4 |
| | | | 2000 | 4 | 7.9 | 7.94 | | | .73 | 6.6 |
| Clinton, WI | May 1999 | 1 | 2000 | 4 | 7.2 | 6.5 | | | .3 | 2.6 |
| | | | 2001 | 4 | 5.2 | 5.3 | | | .4 | 4.3 |
| Arlington, WI | April 1998 | 1 | 1999 | 4 | 6.12 | | 5.35 | 5.12 | .51 | 5.9 |
| | | | 2000 | 4 | 7.45 | | 5.96 | 5.85 | .40 | 4.1 |
| | | | 2001 | 4 | 9.10 | | 7.30 | 6.93 | .54 | 4.5 |
| Manawa, WI | May 2000 | 1 | 2001 | 1 | 1.80 | 1.60 | | | .24 | 7.7 |
| Lacrosse, WI | April 2001 | 1 | 2002 | 4 | 7.97 | — | — | 5.91 | .56 | 3.2 |
| Ames, IA | April 2001 | 1 | 2002 | 4 | 9.0 | 8.0 | — | 7.7 | .37 | — |
| Ithaca, NY | April 2001 | 1 | 2002 | 3 | 6.46 | — | 6.01 | 5.68 | .39 | 5.1 |
| Landisville, PA | April 2001 | 1 | 2002 | 5 | 5.81 | — | 5.07 | 5.31 | .59 | 7.6 |
| Rock Springs, PA | April 2001 | 1 | 2002 | 4 | 6.3 | — | 5.30 | 5.03 | .55 | 6.6 |

| | | | | Mean Annual Yield | | |
|---|---|---|---|---|---|---|
| | Number of Years Harvested | Total Number of Harvests | This Variety | | | |
| Ck 2 Comparison | 6 | 21 | 6.23 | 5.90 | | |
| Ck 3 Comparison | 6 | 24 | 6.87 | | 5.83 | |
| Ck 4 Comparison | 8 | 32 | 7.28 | | | 5.94 |

TABLE 14

Persistence Summary of HybriForce ®-420/Wet

| | | | | | % Stand | | | | |
|---|---|---|---|---|---|---|---|---|---|
| | | | | | | Check Varieties | | | |
| Test Location | Syn Gen | Date Seeded Mo/Yr | Number of Years Harvested | Number of Harvests | Date of Readings (Mo/Yr) Initial/Final | This Variety Initial/Final | Magnum V Initial/Final | Magnum IV Initial/Final | LSD .05 | CV % |
| Clinton, WI | 1 | May 1998 | 3 | 10 | June 1998/May 2001 | 100/85 | 100/83 | 100/87 | 8.6 | 13.9 |
| Clinton, WI | 1 | May 1999 | 3 | 10 | June 1999/October 2001 | 100/90 | 100/90 | 100/90 | 1.2 | 1.0 |
| Marsh, WI | 1 | May 1998 | 3 | 7 | June 1998/May 2000 | 100/80 | 100/80 | 100/79 | 8.8 | 6.3 |
| Marsh, WI | 1 | May 1999 | 3 | 7 | June 1999/October 2001 | 100/99 | 100/99 | 100/98 | 2.5 | 1.5 |
| Spencer, WI | 1 | May 1998 | 2 | 6 | June 1998/May 2000 | 100/68 | 100/67 | 100/65 | 20 | 19 |
| Johns, WI | 1 | May 1999 | 2 | 6 | June 1999/May 2001 | 100/73 | 100/73 | 100/73 | 21 | 17 |

TABLE 15

Winter survival summary of HybriForce ®-420/Wet

| | | Date | Date | | Winter Survival Rating | | | | | | | |
|---|---|---|---|---|---|---|---|---|---|---|---|---|
| | | | | | | | Check Class | | | | | LSD |
| Test Location | Syn Gen | Planted (Mo/Yr) | Measured (Mo/Yr) | This Variety | 1 | 2 | 3 | 4 | 5 | 6 | .05 | CV % |
| Clinton, WI | 1 | May 2000 | May 2001 | 1.6 | 1.4 | 2.1 | 2.5 | 3.0 | 4.4 | 6.0 | .45 | 8.9 |
| Clinton, WI | 1 | May 2001 | May 2002 | 2.2 | 1.2 | 2.2 | 2.8 | 3.5 | 4.1 | 5.8 | .60 | 2.0 |

Note the check variety used for each class (X). Also indicate the winter survival class to which this variety is most similar {X}.

| 1 { } | 2 {X} | 3 { } | 4 { } | 5 { } | 6 { } |
|---|---|---|---|---|---|
| Extremely Winter hardy | Very Winter hardy | Moderately Winter hardy | Low Winter hardy | Winter hardy | Non-Winter hardy |
| ( ) Beaver | ( ) OACMinto | ( ) Apica | ( ) Fortress | ( ) Archer | (X) CUF 101 |
| ( )Maverick | (X) Vernal | (X) Dart | ( ) G2852 | ( ) S. Special | ( ) Moapa 69 |
| (X) Norseman | ( ) 526 | ( ) Ranger | (X) WL 316 | (X) Sutter | ( ) 5929 |

TABLE 16

Flower color of HybriForce ®-420/Wet
A. Flower color at full bloom. Male Syn. generation observed 2, Female generation 1
(See USDA Agriculture Handbook No. 424 - A System for Visually Classifying Alfalfa Flower Color.)

Male

90 % Purple   Trace % Cream   Trace % Yellow   10 % Variegated   Trace % White

Female

90 % Purple   Trace % Cream   Trace % Yellow   10 % Variegated   Trace % White

TABLE 17

Percent hybridism of HybriForce ®-420/Wet $$\% \text{ Hybridism} = \frac{1 - \text{P.P.I. (Hybrid and Non-hybrid)}}{1 - \text{P.P.I. (Hybrid)}} - \text{P.P.I. (AxB)} \times .595$$

$$83.7 = \frac{1 - (.742)}{1 - (.71)} - (.0857) \times .595$$

As the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A *Medicago sativa* or cultivated alfalfa seed deposited as ATCC Accession Number PTA-5858.

2. A *Medicago sativa* hybrid or cultivated alfalfa plant grown from seed deposited as ATCC Accession Number PTA-5858.

3. Pollen from the plant of claim 2.

4. An ovule from the plant of claim 2.

5. A vegetative cutting, callus or tissue culture produced from the plant of claim 2.

6. A clonal plant produced from the vegetative cutting, callus or tissue culture of claim 5, said clonal plant having all the physiological and morphological characteristics of a *Medicago sativa* plant grown from the seed deposited as ATCC Accession Number PTA-5858.

* * * * *